(12) United States Patent
Moghaddam et al.

(10) Patent No.: US 11,040,983 B1
(45) Date of Patent: Jun. 22, 2021

(54) COCRYSTAL OF VARENICLINE AND OXALIC ACID, PHARMACEUTICAL COMPOSITION THEREOF, AND METHODS OF USE THEREOF

(71) Applicant: Almatica Pharma LLC, Morristown, NJ (US)

(72) Inventors: Siya Moghaddam, Morris Plains, NJ (US); Venkat Reddy Alla, Hyderabad (IN); Raghumitra Alla, Hyderabad (IN); Srinivas Reddy Mallepalli, Hyderabad (IN)

(73) Assignee: ALMATICA PHARMA LLC, Morristown, NJ (US)

( * ) Notice: Subject to any disclaimer, the term of this patent is extended or adjusted under 35 U.S.C. 154(b) by 0 days.

(21) Appl. No.: 16/993,439

(22) Filed: Aug. 14, 2020

(51) Int. Cl.
*C07D 487/18* (2006.01)

(52) U.S. Cl.
CPC ........ *C07D 487/18* (2013.01); *C07B 2200/13* (2013.01)

(58) Field of Classification Search
None
See application file for complete search history.

(56) References Cited

U.S. PATENT DOCUMENTS

| 6,410,550 B1 | 6/2002 | Coe et al. |
| 8,440,825 B2 | 5/2013 | Winter et al. |

FOREIGN PATENT DOCUMENTS

| EP | 3400964 A1 | 11/2018 |
| IN | 0908CHE2009 | 4/2012 |
| IN | 2983MUM2009 | 7/2014 |
| KR | 20160126697 A | 11/2016 |
| WO | 2011110954 A1 | 9/2011 |
| WO | 2018154395 A2 | 8/2018 |

OTHER PUBLICATIONS

International Search Report and Written Opinion dated Apr. 13, 2021 in International Application No. PCT/US2020/046304.

*Primary Examiner* — Brian J Davis
(74) *Attorney, Agent, or Firm* — Panitch Schwarze Belisario & Nadel LLP

(57) ABSTRACT

Provided is a cocrystal of varenicline and oxalic acid. In particular, provided is a cocrystal of varenicline and oxalic acid of formula (I) having a molar ratio of varenicline to oxalic acid of 1:1.5. Also provided is a process for preparing the cocrystal, a pharmaceutical composition containing the cocrystal and a method of using the cocrystal and pharmaceutical composition, such as for reducing nicotine addiction or tobacco use.

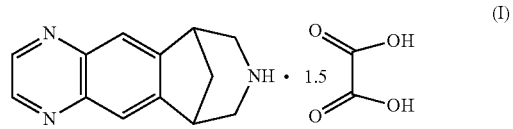

13 Claims, 1 Drawing Sheet

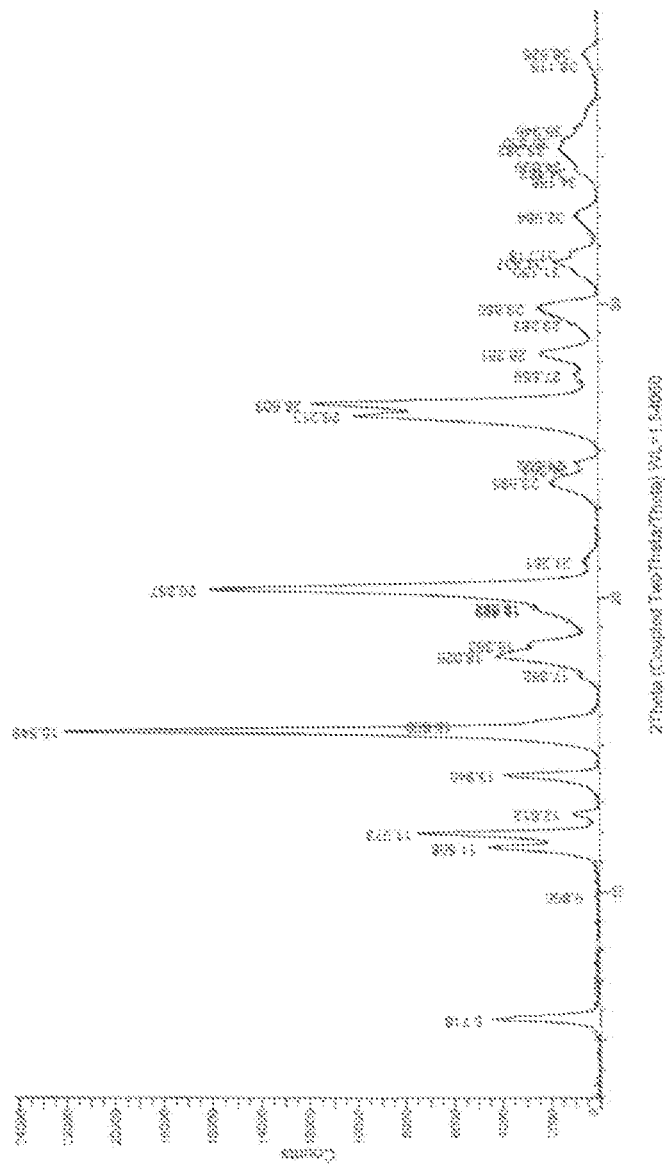

COCRYSTAL OF VARENICLINE AND OXALIC ACID, PHARMACEUTICAL COMPOSITION THEREOF, AND METHODS OF USE THEREOF

BACKGROUND OF THE INVENTION

The compound 7,8,9,10-tetrahydro-6,10-methano-6H-pyrazino[2,3-h][3]benzazepine, commonly known as varenicline, has the following chemical structure:

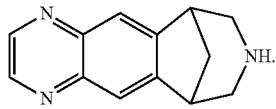 [SMILES: c1cnc2cc3c(cc2n1)C1CNCC3C1]

Varenicline and its pharmaceutically acceptable acid addition salts are described in U.S. Pat. No. 6,410,550. Varenicline is a partial agonist selective for $\alpha_4\beta_2$ nicotinic acetylcholine receptor subtypes. Varenicline tartrate is approved by the U.S. Food and Drug Administration (FDA) for use as an aid to smoking cessation treatment and is marketed as Chantix®.

Additional salt and crystalline salt forms of varenicline, such as fumarate, succinate, and oxalate forms, have been described in, for example, U.S. Pat. No. 8,440,825; Korean Patent Application Publication KR 10-2016-0126697; Indian Patent Application Publication IN 0908/CHE/2009; and Indian Patent Application Publication IN 2983/MUM/2009.

However, different crystalline forms of a molecule can have very different properties, such as solubility, dissolution rate, bioavailability, hygroscopic behavior, manufacturability, etc. rendering some forms more suitable as active ingredients in drug substances as compared to other forms.

BRIEF DESCRIPTION OF THE INVENTION

Accordingly, there is a need for novel solid forms of varenicline. Provided herein is a novel cocrystal of varenicline and oxalic acid.

In one general aspect, provided is a cocrystal of varenicline and oxalic acid of formula (I):

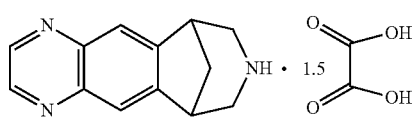

wherein a molar ratio of varenicline to oxalic acid in the cocrystal is 1:1.5.

In some embodiments, provided is a cocrystal of varenicline and oxalic acid characterized by an X-ray powder diffraction (XRPD) spectrum comprising diffraction peaks at diffraction angles (2θ±0.2°) of 5.718, 11.508, 11.973, 13.946, 15.549, 15.699, 18.026, 20.357, 26.213, and 26.603.

In some embodiments, provided is a cocrystal of varenicline and oxalic acid having an X-ray powder diffraction (XRPD) spectrum as shown in The FIGURE.

In another aspect, provided is a process for producing a cocrystal of varenicline and oxalic acid as described herein, comprising:

(a) dissolving varenicline free base in a solvent, heating, and cooling to form a varenicline solution;
(b) dissolving oxalic acid dihydrate in the solvent to form an oxalic acid solution;
(c) adding the oxalic acid solution to the varenicline solution to form a reaction mixture; and
(d) stirring the reaction mixture at room temperature to precipitate the cocrystal.

In another aspect, provided is a pharmaceutical composition comprising a cocrystal of varenicline and oxalic acid as described herein, and a pharmaceutically acceptable carrier.

In yet another aspect, provided is a method of reducing nicotine addiction or tobacco use in a subject in need thereof, the method comprising administering to the subject a pharmaceutical composition as described herein.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the drawings:

The FIGURE shows the X-ray powder diffraction (XRPD) spectrum of the cocrystal of varenicline and oxalic acid obtained in Example 2.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the disclosure. Such discussion is not an admission that any or all of these matters form part of the prior art with respect to the disclosure.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise stated, any numerical value is to be understood as being modified in all instances by the term "about." Thus, a numerical value typically includes ±10% of the recited value. For example, the recitation of a temperature such as "10° C." includes 9° C. and 11° C. As used herein, the use of a numerical range expressly includes all possible subranges, all individual numerical values within that range, including integers within such ranges and fractions of the values unless the context clearly indicates otherwise.

In one general aspect, provided herein is a cocrystal of varenicline and oxalic acid of formula (I):

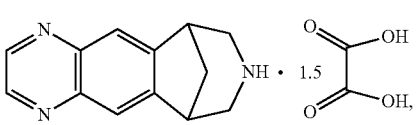

wherein a molar ratio of varenicline to oxalic acid in the cocrystal is 1:1.5.

Cocrystal

As used herein, "varenicline" and "varenicline free base" refer to a compound of formula (II):

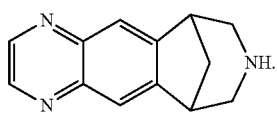

Varenicline is a benzazepine derivative that is a partial agonist of the nicotinic acetylcholine receptor (nAChR) subtype α4β2. Varenicline has the molecular formula $C_{13}H_{13}N_3$ and is known by the following chemical names: 6,7,8,9-tetrahydro-6,10-methano-6H-pyrazino(2,3-h)benzazepine and 7,8,9,10-tetrahydro-6,10-methano-6H-pyrazino-[2,3-h][3]benzazepine.

Varenicline can be prepared by any method known in the art in view of the present disclosure. An exemplary and non-limiting process for synthesizing varenicline free base, which can subsequently be used to form a cocrystal as described herein, is shown in Scheme 1.

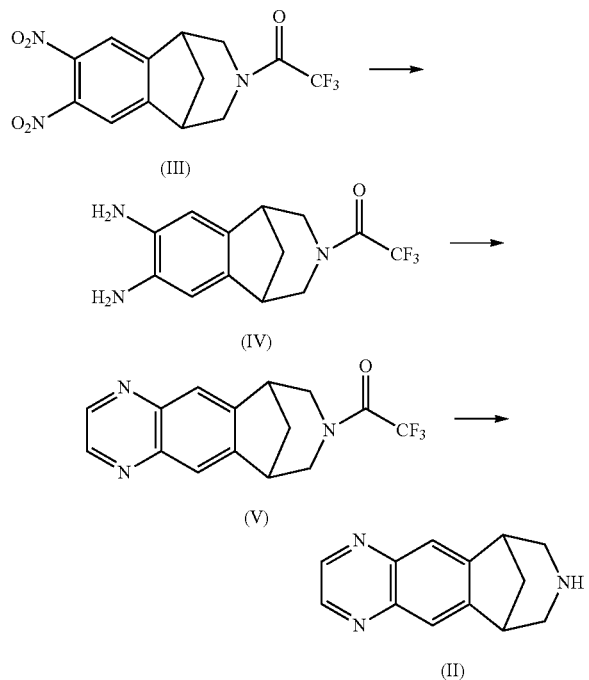

Scheme 1: Synthesis of Varenicline Free Base

As shown in Scheme 1, the dinitro compound (III) is reduced under hydrogen gas pressure in the presence of a palladium on carbon catalyst in a suitable organic solvent. After completion of the reduction reaction, the Pd/C catalyst is separated by filtration and the filtrate is concentrated to yield the dianiline compound (IV). The dianiline compound (IV) is then cyclized using glyoxal or a glyoxal derivative in water or a polar solvent, such as acetonitrile, tetrahydrofuran (THF), dimethylformamide (DMF), or dimethylsulfoxide (DMSO) with 40% aqueous glyoxal solution in a suitable organic solvent under nitrogen atmosphere. Once the cyclization reaction is complete, the reaction mixture is concentrated, mixed with water, and acidified by addition of dilute acid, followed by extraction. The organic layer is washed and concentrated, and the cyclized compound (V) is isolated. The 2,2,2-trifluoroethanone nitrogen protecting group is then removed by treating the cyclized compound (V) with an aqueous alkali or alkaline earth metal hydroxide (e.g., NaOH) in a solvent mixture of water and lower alkanol (e.g., methanol) or a water immiscible solvent (e.g., toluene or dichloromethane). The reaction mixture is then extracted, and the organic layer is washed with water, dried, and concentrated to yield varenicline free base (compound (II)).

Alternative procedures for synthesizing varenicline free base and modifications to the procedure shown in Scheme 1 that can be employed are described in, e.g., U.S. Pat. No. 6,410,550, U.S. Patent Application Publication No. 2009/0318695, U.S. Patent Application Publication No. 2008/0275051, and International Patent Application Publication WO2018163190. For example, the process shown in Scheme 1 can be modified to include a further purification step of the cyclized compound (V) following cyclization with glyoxal or a glyoxal derivative by combining the cyclized compound with an acid (e.g., HCl, HBr, HI, $H_2SO_4$) and extracting the reaction mixture prior to removal of the 2,2,2-trifluoroethanone nitrogen protecting group.

As used herein, the term "oxalic acid" refers to a dicarboxylic acid compound having the formula $C_2H_2O_4$ and the structure:

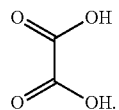

Oxalic acid can exist as a dihydrate, referred to as "oxalic acid dihydrate," which has the formula $C_2H_2O_4 \cdot 2H_2O$.

As used herein, the term "cocrystal" refers to a solid form composed of at least two components present in a stoichiometric ratio which does not equate to a simple salt. Cocrystals can exist in crystalline form or amorphous form, and when in crystalline form, the components of a cocrystal typically form a unique crystalline structure having unique properties. The components of a cocrystal typically include an active pharmaceutical ingredient (API) or drug component and at least one further component which is not a solvent, i.e., a coformer molecule. For example, a cocrystal can be composed of two components, such as an active pharmaceutical ingredient (API) and a coformer. A "polymorph" is a crystalline solid form of one or more components having a particular arrangement and/or conformation of the component(s) in the crystal lattice. Different polymorphs differ in solid-state structure, but not in the chemical structure of the component(s). Cocrystals can exist in different crystalline forms and thus can exhibit polymorphism. In particular, "cocrystal of varenicline and oxalic acid," "cocrystal of varenicline oxalate," and "varenicline oxalate cocrystal" refer to a solid form composed of varenicline (API) and oxalic acid (coformer). A cocrystal of varenicline and oxalic acid can be in amorphous form or crystalline form, and is preferably in crystalline form, i.e., a polymorph.

In some embodiments, provided is a cocrystal of varenicline and oxalic acid in which a molar ratio of varenicline to oxalic acid in the cocrystal is 1:1.5.

In some embodiments, provided is a polymorph or crystalline form of a cocrystal of varenicline and oxalic acid in which a molar ratio of varenicline to oxalic acid in the cocrystal is 1:1.5.

In some embodiments, provided is a cocrystal of varenicline and oxalic acid characterized by an X-ray powder diffraction (XRPD) spectrum comprising diffraction peaks at diffraction angles (2θ±0.2°) of 5.718, 11.508, 11.973, 13.946, 15.549, 15.699, 18.026, 20.357, 26.213, and 26.603.

In some embodiments, provided is a cocrystal of varenicline and oxalic acid characterized by an X-ray powder diffraction (XRPD) spectrum comprising the following d-values (Å) at the indicated diffraction angles (2θ)±0.2°:

| Angle (2θ ± 0.2°) | d value (Å) |
| --- | --- |
| 5.718 | 15.44416 |
| 11.508 | 7.68327 |
| 11.973 | 7.38574 |
| 13.946 | 6.34515 |
| 15.549 | 5.69431 |
| 15.699 | 5.64011 |
| 18.026 | 4.91703 |
| 20.357 | 4.35895 |
| 26.213 | 3.39696 |
| 26.603 | 3.34809 |

In some embodiments, provided is a cocrystal of varenicline and oxalic acid characterized by an X-ray powder diffraction (XRPD) spectrum comprising diffraction peaks at diffraction angles (2θ±0.2°) of 5.718, 11.508, 11.973, 13.946, 15.549, 15.699, 18.026, 20.357, 26.213, and 26.603, and further comprising diffraction peaks at diffraction angles (2θ±0.2°) of 9.866, 12.612, 17.382, 18.383, 19.602, 19.682, 21.251, 24.351, 23.895, 24.502, 27.559, 28.281, 29.283, 29.850, 31.150, 31.437, 31.781, 32.984, 34.188, 34.487, 34.699, 35.282, 35.530, 35.946, 38.118, and 38.526.

In some embodiments, provided is a cocrystal of varenicline and oxalic acid characterized by an X-ray powder diffraction (XRPD) spectrum comprising the following d-values (Å) at the indicated diffraction angles (2θ)±0.2°:

| Angle (2θ ± 0.2°) | d value (Å) |
| --- | --- |
| 5.718 | 15.44416 |
| 9.866 | 8.95802 |
| 11.508 | 7.68327 |
| 11.973 | 7.38574 |
| 12.612 | 7.01298 |
| 13.946 | 6.34515 |
| 15.549 | 5.69431 |
| 15.699 | 5.64011 |
| 17.382 | 5.09785 |
| 18.026 | 4.91703 |
| 18.383 | 4.82231 |
| 19.602 | 4.52510 |
| 19.682 | 4.50692 |
| 20.357 | 4.35895 |
| 21.251 | 4.17766 |
| 24.351 | 3.65236 |
| 23.895 | 3.72102 |
| 24.502 | 3.63011 |
| 26.213 | 3.39696 |
| 26.603 | 3.34809 |
| 27.559 | 3.23398 |
| 28.281 | 3.15305 |
| 29.283 | 3.04748 |
| 29.850 | 2.99078 |
| 31.150 | 2.86894 |
| 31.437 | 2.84335 |
| 31.718 | 2.81886 |
| 32.984 | 2.71348 |
| 34.188 | 2.62060 |
| 34.487 | 2.59858 |
| 34.699 | 2.58317 |
| 35.282 | 2.54182 |
| 35.530 | 2.52461 |
| 35.946 | 2.49634 |
| 38.118 | 2.35899 |
| 38.526 | 2.33492 |

In some embodiments, provided is a cocrystal of varenicline and oxalic acid characterized by an X-ray powder diffraction (XRPD) spectrum as shown in The FIGURE.

In some embodiments, provided is a cocrystal of varenicline and oxalic acid having a purity of at least 99.8% relative peak area as determined by high performance liquid chromatography (HPLC).

A cocrystal of varenicline and oxalic acid can be characterized by any method known in the art in view of the present disclosure including, but not limited to, Fourier Transform Infrared (FTIR) spectroscopy, X-ray powder diffraction (XRPD), differential scanning calorimetry (DSC), high performance liquid chromatography (HPLC), etc.

Process

In another general aspect, provided is a process for producing a cocrystal of varenicline and oxalic acid as provided herein. According to embodiments of the application, a process for producing such a cocrystal comprises combining varenicline free base (preferably a varenicline solution in isopropanol) with a solution of oxalic acid dihydrate (preferably in isopropanol) and precipitating the cocrystal.

In an embodiment, provided is a process for producing a cocrystal of varenicline and oxalic acid comprising:
(a) dissolving varenicline free base in a solvent, heating, and cooling to form a varenicline solution;
(b) dissolving oxalic acid dihydrate in the solvent to form an oxalic acid solution;
(c) adding the oxalic acid solution to the varenicline solution to form a reaction mixture; and
(d) stirring the reaction mixture at room temperature to precipitate the cocrystal.

Varenicline free base used in a process for preparing a cocrystal as described herein can be synthesized according to any method known in the art in view of the present disclosure. Preferably, oxalic acid dihydrate is used in the process. However, it is also within the scope of the disclosure to utilize anhydrous oxalic acid, provided that it has the desired solubility.

The preferred solvent for forming the varenicline solution and for forming the oxalic acid solution is isopropanol. However, it is also within the scope of the disclosure to utilize other solvents, including other alcohols, provided that they provide the desired solubility for the oxalic acid dihydrate and the varenicline free base.

According to embodiments of the application, a solution of varenicline free base in isopropanol is prepared by dissolving varenicline free base in isopropanol and heating to a temperature of about 35-40° C. After stirring at about 35-40° C. for about 15-20 minutes to produce a clear solution, the mixture is filtered (such as with a micron filter), washed with (preferably warm) isopropanol, and cooled, preferably to about 25 to 30° C., all under a nitrogen atmosphere.

Separately, a solution of oxalic acid dihydrate in isopropanol is prepared by dissolving oxalic acid dihydrate in isopropanol at room temperature, stirring, and filtering (such as through a micron filter), and washing with isopropanol.

The solution of oxalic acid dihydrate/isopropanol is then slowly (such as over a period of 45 to 60 minutes) added to the varenicline/isopropanol solution, preferably at a temperature of about 25-30° C. under a nitrogen atmosphere, such that a ratio of oxalic acid to varenicline free base in the reaction mixture is at least about 2:1. While it is within the scope of the disclosure the employ a greater excess of oxalic acid to varenicline free base in the reaction mixture, there are no benefits to employing such larger amounts.

The resulting reaction mixture is then stirred, preferably at about 25-30° C. in a nitrogen atmosphere, to precipitate the cocrystal.

It is preferred that the oxalic acid solution be added to the varenicline solution, but it is also within the scope of the disclosure to perform the addition in the reverse order. Further, if the oxalic acid solution is added too quickly, the yield and quality of the resulting cocrystal product may be affected.

In some embodiments, a process further comprises isolating the cocrystal from the reaction mixture. The precipitated cocrystal can be isolated from the reaction mixture by any method known in the art in view of the present disclosure, e.g., filtration. The cocrystal can be washed with a suitable organic solvent, preferably isopropanol, and dried, e.g., under vacuum or in an inert atmosphere.

More specifically, the cocrystal may be isolated from the reaction mixture by filtration, washed with isopropanol and dried under nitrogen to remove the excess water, then further dried by heating such as by heating to successively higher temperatures such as about 40-45°, then about 70-75° C., then about 85-90° C. Isopropanol is the preferred solvent for washing the cocrystal because of its ability to dissolve and remove unreacted starting materials. Preferably, the residual water in the cocrystal is ≤1.0% w/w, more preferably ≤0.5% w/w using a Karl-Fischer titration method.

Compositions

In another general aspect, provided is a pharmaceutical composition comprising a cocrystal of varenicline and oxalic acid as described herein.

Compositions can also comprise a pharmaceutically acceptable carrier. A pharmaceutically acceptable carrier is non-toxic and should not interfere with the efficacy of the active ingredient, e.g., varenicline. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For solid oral preparations, for example, powders, capsules, caplets, gelcaps and tablets, suitable carriers and additives include starches, sugars, diluents, granulating agents, lubricants, binders, disintegrating agents and the like.

Compositions can be formulated in any matter suitable for administration to a subject to facilitate administration and improve efficacy, including, but not limited to, oral (enteral) administration and parenteral injections, preferably for oral administration. Compositions suitable for oral administration include tablets, capsules, etc.

In yet another aspect, provided is a method of preparing a pharmaceutical composition comprising combining a cocrystal of varenicline and oxalic acid as described herein, with at least one pharmaceutically acceptable carrier. Pharmaceutical compositions can be prepared by any method known in the art in view of the present disclosure, and one of ordinary skill in the art will be familiar with such techniques used to prepare pharmaceutical compositions, such as by conventional pharmaceutical compounding techniques, including but not limited to, conventional admixing, dissolving, granulating, emulsifying, encapsulating, entrapping or lyophilizing processes.

Methods of Use

In yet another aspect, provided is a method of reducing nicotine addiction or tobacco use in a subject in need thereof, comprising administering to the subject a cocrystal of varenicline and oxalic acid as described herein or pharmaceutical composition comprising a cocrystal of varenicline and oxalic acid as described herein.

In preferred embodiments, a pharmaceutical composition is formulated for oral administration, e.g., a tablet, and is administered to a subject orally.

EXAMPLES

The following examples of the application are to further illustrate the nature of the application. It should be understood that the following examples do not limit the application and the scope of the application is to be determined by the appended claims.

Example 1: Synthesis of Varenicline Free Base

Varenicline free base was synthesized according to Scheme 2 shown below.

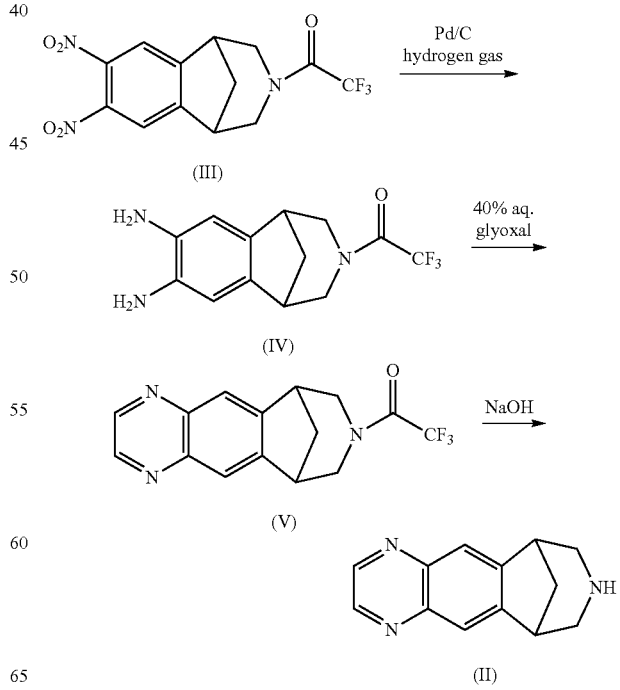

1-(7,8-dinitro-4,5-dihydro-1H-1,5-methanobenzo[d]azepin-3(2H)-yl)-2,2,2-trifluoroethanone (III) was reduced using 10% palladium on carbon (Pd/C) in the presence of triethylamine in ethyl acetate solvent under hydrogen gas pressure until completion of the reduction reaction. After completion of the reaction, the Pd/C catalyst was separated from the reaction mixture by filtration, and the filtrate was concentrated and isolated in isopropyl alcohol to yield 1-7,8-diamino-4,5-dihydro-1H-1,5-methanobenzo[d]azepin-3(2H)-yl)-2,2,2-trifluoroethanone (IV).

1-7,8-diamino-4,5-dihydro-1H-1,5-methanobenzo[d]azepin-3(2H)-yl)-2,2,2-trifluoroethanone (IV) was reacted with 40% aqueous glyoxal solution in acetonitrile with nitrogen blanketing. After completion of the reaction, the reaction mixture was concentrated and then demineralized (DM) water was added, followed by dilute hydrochloric acid (HCl) solution to acidify the mixture. The mixture was extracted with ethyl acetate and the organic layer was washed with DM water. The organic layer was treated with bleaching earth and then concentrated. Isolation in cyclohexane and isopropanol yielded 1-(9,10-dihydro-6H-6,10-methanoazepino[4,5-g]quinoxaline-8(7H)-yl)-2,2,2,-trifluoroethanone (V).

1-(9,10-dihydro-6H-6,10-methanoazepino[4,5-g]quinoxaline-8(7H)-yl)-2,2,2,-trifluoroethanone (V) was reacted with sodium hydroxide in a mixture of DM water and methanol. After completion of the reaction, the reaction mixture was concentrated, and sodium chloride solution was added. The resulting mixture was extracted with dichloromethane and the organic layer was washed with DM water. The organic layer was dried with sodium sulphate and then concentrated. Isolation in ethyl acetate yielded 7,8,9,10-tetrahydro-6,10-methano-6H-pyrazino[2,3-h][3]benzazepine (II) (varenicline free base).

Example 2: Preparation of Cocrystal of Varenicline and Oxalic Acid

A cocrystal of varenicline and oxalic acid was prepared by mixing varenicline free base with oxalic acid in isopropanol as shown in Scheme 3.

Scheme 3: Preparation of Cocrystal

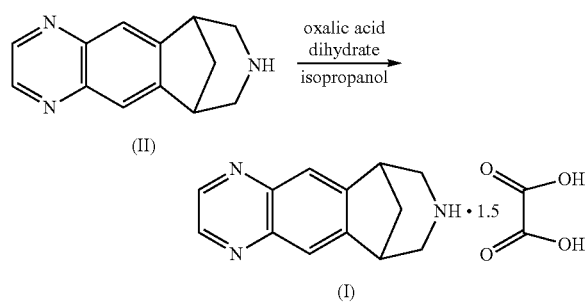

100.0 g (0.473 mol) of varenicline base was dissolved in 1000 ml of isopropanol, heated to 35-40° C., then stirred at 35-40° C. under a nitrogen atmosphere for 15-20 minutes, filtered through a micron filler, washed with 50 ml of warm isopropanol at 35-40° C., then cooled under nitrogen to 25-30° C. Separately, a solution of oxalic acid dihydrate in isopropanol was prepared by dissolving 120 g (0.952 mol) oxalic acid dihydride in 800 ml isopropanol at room temperature, stirring, filtering through a micron filter, and washing with 50 ml isopropanol. The oxalic acid solution was then slowly added to the varenicline/isopropanol solution over a period of 45 to 60 minutes at 25-30° C. under a nitrogen atmosphere to produce a reaction mixture, then stirred for 30-45 minutes at 25-30° C. to precipitate the cocrystal. The cocrystal was then filtered, washed with isopropanol, dried at 25-30° C., then further dried by heating under nitrogen at 40-45° C., then at 70-75° C., then at 85-90° C.

The resulting cocrystal has a molecular formula of $C_{13}H_{13}N_3 \cdot 1.5(C_2H_2O_4)$ and molecular weight of 346.31. The resulting cocrystal was analyzed by X-ray powder diffraction. The X-ray powder diffraction (XRPD) spectrum is shown in The FIGURE and the peak list is shown in Table 1.

TABLE 1

Peak List of XRPD Spectrum of Varenicline Oxalate Cocrystal

| Angle (2θ ± 0.2°) | d value (Å) | Relative Intensity (%) |
|---|---|---|
| 5.718 | 15.44416 | 19.8 |
| 9.866 | 8.95802 | 0.6 |
| 11.508 | 7.68327 | 20.06 |
| 11.973 | 7.38574 | 32.9 |
| 12.612 | 7.01298 | 4.8 |
| 13.946 | 6.34515 | 17.0 |
| 15.549 | 5.69431 | 100.0 |
| 15.699 | 5.64011 | 25.2 |
| 17.382 | 5.09785 | 3.0 |
| 18.026 | 4.91703 | 19.3 |
| 18.383 | 4.82231 | 13.3 |
| 19.602 | 4.52510 | 11.9 |
| 19.682 | 4.50692 | 12.1 |
| 20.357 | 4.35895 | 73.7 |
| 21.251 | 4.17766 | 2.5 |
| 24.351 | 3.65236 | 3.1 |
| 23.895 | 3.72102 | 8.6 |
| 24.502 | 3.63011 | 3.9 |
| 26.213 | 3.39696 | 46.5 |
| 26.603 | 3.34809 | 53.8 |
| 27.559 | 3.23398 | 4.5 |
| 28.281 | 3.15305 | 10.9 |
| 29.283 | 3.04748 | 4.6 |
| 29.850 | 2.99078 | 11.4 |
| 31.150 | 2.86894 | 4.5 |
| 31.437 | 2.84335 | 7.8 |
| 31.718 | 2.81886 | 5.2 |
| 32.984 | 2.71348 | 3.8 |
| 34.188 | 2.62060 | 1.2 |
| 34.487 | 2.59858 | 3.3 |
| 34.699 | 2.58317 | 4.2 |
| 35.282 | 2.54182 | 7.5 |
| 35.530 | 2.52461 | 6.4 |
| 35.946 | 2.49634 | 4.0 |
| 38.118 | 2.35899 | 1.3 |
| 38.526 | 2.33492 | 2.7 |

The obtained varenicline oxalate cocrystal was further analyzed by high performance liquid chromatography (HPLC) to determine the purity and oxalic acid content. Based on the HPLC analysis, the varenicline oxalate cocrystal had a purity of 99.8% (w/w) and an oxalic acid content of 37.9% (w/w) (on anhydrous basis). Based on these results, the molar ratio of varenicline to oxalic acid was determined to be 1:1.5. The residual water in the cocrystal was ≤1.0% w/w using Karl-Fischer titration, confirming that water was not embedded in the crystal as a solvate but on top of the crystal. Additionally, pKa, IR, and DSC studies confirmed the 1:1.5 ratio by comparison with a 1:1 varenicline oxalate sample.

It will be appreciated by those skilled in the art that changes could be made to the embodiment described above without departing from the broad inventive concepts thereof.

Also, based on this disclosure, a person of ordinary skill in the art would further recognize that the relative proportions of the components illustrated above could be varied without departing from the spirit and scope of the invention. It is understood, therefore, that this invention is not limited to that particular embodiment disclosed, but it is intended to cover modifications within the spirit and scope of the present invention as defined by the appended claims.

We claim:

1. A cocrystal of varenicline and oxalic acid of formula (I):

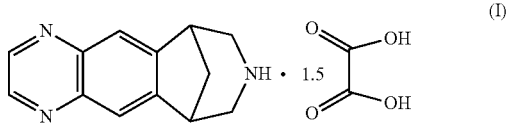 [SMILES: c1cnc2cc3c(cc2n1)C1CNCC3C1 ; O=C(O)C(=O)O]

wherein a molar ratio of varenicline to oxalic acid in the cocrystal is 1:1.5.

2. The cocrystal of claim 1, characterized by an X-ray powder diffraction (XRPD) spectrum comprising diffraction peaks at diffraction angles (2θ±0.2°) of 5.718, 11.508, 11.973, 13.946, 15.549, 15.699, 18.026, 20.357, 26.213, and 26.603.

3. The cocrystal of claim 2, further comprising diffraction peaks at diffraction angles (2θ±0.2°) of 9.866, 12.612, 17.382, 18.383, 19.602, 19.682, 21.251, 24.351, 23.895, 24.502, 27.559, 28.281, 29.283, 29.850, 31.150, 31.437, 31.781, 32.984, 34.188, 34.487, 34.699, 35.282, 35.530, 35.946, 38.118, and 38.526.

4. The cocrystal of claim 1, wherein the cocrystal has an X-ray powder diffraction (XRPD) spectrum as shown in The FIGURE.

5. A process for producing the cocrystal of claim 1, the process comprising:
  (a) dissolving varenicline free base in a solvent, heating, and cooling to form a varenicline solution;
  (b) dissolving oxalic acid dihydrate in the solvent to form an oxalic acid solution;
  (c) adding the oxalic acid solution to the varenicline solution to form a reaction mixture; and
  (d) stirring the reaction mixture at room temperature to precipitate the cocrystal.

6. A process for producing the cocrystal of claim 2, the process comprising:
  (a) dissolving varenicline free base in a solvent, heating, and cooling to form a varenicline solution;
  (b) dissolving oxalic acid dihydrate in the solvent to form an oxalic acid solution;
  (c) adding the oxalic acid solution to the varenicline solution to form a reaction mixture; and
  (d) stirring the reaction mixture at room temperature to precipitate the cocrystal.

7. A process for producing the cocrystal of claim 4, the process comprising:
  (a) dissolving varenicline free base in a solvent, heating, and cooling to form a varenicline solution;
  (b) dissolving oxalic acid dihydrate in the solvent to form an oxalic acid solution;
  (c) adding the oxalic acid solution to the varenicline solution to form a reaction mixture; and
  (d) stirring the reaction mixture at room temperature to precipitate the cocrystal.

8. A pharmaceutical composition comprising the cocrystal of claim 1 and a pharmaceutically acceptable carrier.

9. A pharmaceutical composition comprising the cocrystal of claim 2 and a pharmaceutically acceptable carrier.

10. A pharmaceutical composition comprising the cocrystal of claim 4 and a pharmaceutically acceptable carrier.

11. A method of reducing nicotine addiction or tobacco use in a subject in need thereof, the method comprising administering to the subject the pharmaceutical composition of claim 8.

12. A method of reducing nicotine addiction or tobacco use in a subject in need thereof, the method comprising administering to the subject the pharmaceutical composition of claim 9.

13. A method of reducing nicotine addiction or tobacco use in a subject in need thereof, the method comprising administering to the subject the pharmaceutical composition of claim 10.

* * * * *